United States Patent
Barni et al.

[11] Patent Number: 5,841,830
[45] Date of Patent: Nov. 24, 1998

[54] 3D CT FLUOROSCOPY

[75] Inventors: John J. Barni, Mayfield Village; Kenneth L. Freeman, Stow; Gary A. Kaufmann, Hinckley; Darrell M. Smith, Cleveland Heights, all of Ohio

[73] Assignee: Picker International, Inc., Highland Heights, Ohio

[21] Appl. No.: 802,618

[22] Filed: Feb. 19, 1997

[51] Int. Cl.$^6$ ..................................................... A61B 6/03
[52] U.S. Cl. ............................................. 378/15; 378/901
[58] Field of Search .................................. 378/4, 15, 16, 378/901; 600/407, 431

[56] References Cited

U.S. PATENT DOCUMENTS

| | | | |
|---|---|---|---|
| 4,791,934 | 12/1988 | Brunnett | 600/429 |
| 5,274,551 | 12/1993 | Corby, Jr. | 600/433 |
| 5,309,913 | 5/1994 | Kormos et al. | 600/429 |
| 5,333,164 | 7/1994 | Tam | 378/8 |
| 5,396,418 | 3/1995 | Heuscher | 378/15 |
| 5,450,462 | 9/1995 | Toth et al. | 378/16 |
| 5,544,212 | 8/1996 | Heuscher | 378/15 |
| 5,592,523 | 1/1997 | Tuy et al. | 278/19 |
| 5,594,766 | 1/1997 | Tam | 378/4 |
| 5,594,772 | 1/1997 | Toki et al. | 378/114 |
| 5,625,660 | 4/1997 | Tuy | 378/15 |
| 5,708,690 | 1/1998 | Hsieh | 378/4 |

OTHER PUBLICATIONS

Voxel Q Visualization System Advertising Brochure, Picker International, Inc. 1994.

*Primary Examiner*—David P. Porta
*Assistant Examiner*—David Vernon Bruce
*Attorney, Agent, or Firm*—Fay, Sharpe, Beall, Fagan, Minnich & McKee

[57] ABSTRACT

A radiation source which generates a radiation cone-beam (14) and a two-dimensional radiation detector are spiralled continuously around and longitudinally relative to an imaging volume. Image data from the two-dimensional display is reconstructed ($30_1$, $30_2$, ... $30_n$) into a volumetric, physiological image stored in a subject memory (32). During an interventional surgical procedure with a surgical instrument (42), the x-ray source is gated to operate intermittently, e.g., at 60° angular intervals, at a reduced radiation intensity by an x-ray tube control (40). The additional data is reconstructed into a three-dimensional image representation of the surgical instrument and stored in an instrument memory (34). An operator image selection processor (60) causes data retrieval circuits (62a, 62b) to retrieve like slices or other image representations from the subject and instrument memories. The retrieved data is combined (64) such that a resultant human-readable display (68) shows the instrument superimposed on the anatomical image. The surgical instrument volumetric image is continuously updated such that the display represents a real time display of the surgical instrument illustrating its advancement through the imaging region.

16 Claims, 1 Drawing Sheet

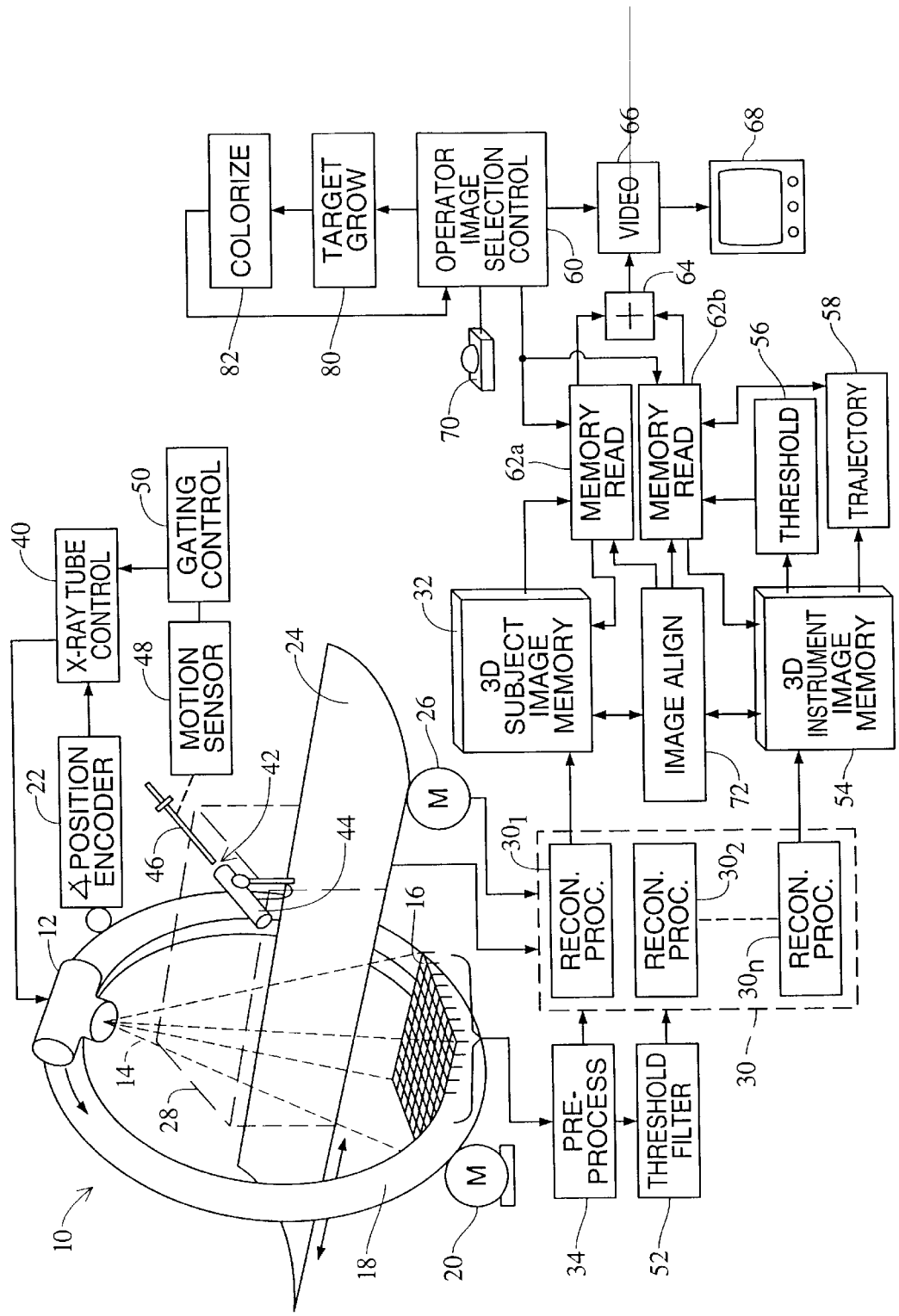

3D CT FLUOROSCOPY

BACKGROUND OF THE INVENTION

The present invention relates to the art of diagnostic imaging. It finds particular application in conjunction with the presentation of real time, three-dimensional computed tomography imaging and will be described with particular reference thereto.

In some operating rooms, such as operating rooms for cardiac catheter procedures, a projection x-ray imaging device is provided in association with the operating table. More specifically, an x-ray tube or generator and an x-ray detector are mounted on a C-arm which is mounted such that the patient passes between the x-ray source and detector. The x-ray source and detector are rotatable and longitudinally displaceable as a unit to select a region and angle for projection imaging. Once the surgeon has positioned the x-ray source and detector in the proper position, the surgeon actuates the x-ray tube to send x-rays through the patient to the x-ray detector for preselected exposure time. The x-rays received by the detector are converted into electronic, video image data of a projection or shadowgraphic image. The projection or shadowgraphic image is displayed on a video monitor which is viewable by the physician.

In the cardiac catheterization procedures, some images are preceded by releasing an x-ray opaque dye into the patient's blood. The resultant shadowgraphic image shows the blood vessels dark. Other images are generated of the catheter within the blood vessels. More specifically, the surgeon advances the catheter into the patient, stops the procedure, and takes an x-ray picture. The x-rays are converted into the electronic projection image and displayed within a few seconds. The surgeon then determines from the projection image how much further to advance the catheter before again stopping the procedure and generating a new image. Multiple monitors are often provided so that the surgeon can view both the most recently generated projection image and earlier images.

One of the drawbacks of these x-ray systems is that the resultant image is a projection or shadowgraphic image. That is, the entire imaged region of the patient is projected onto the x-ray detector and all of the imaged region is compressed into a single plane. If more detailed diagnostic images are required, such images are often taken with a CT scanner or a magnetic resonance imaging device located in another part of the facility. Thus, the 3D diagnostic images are commonly generated sometime earlier before the surgical procedure starts. Because the patient would need to be transported to the CT or MRI machine for further imaging, further images are not generally taken during surgery.

It has been proposed to use a C-magnet magnetic resonance imaging apparatus within an operating room. The magnetic resonance imaging device would be used to generate a three-dimensional diagnostic image. Based on the diagnostic image, a surgical procedure would be commenced, such as a biopsy. From time to time during the biopsy procedure, additional 3D diagnostic images could be generated to monitor the advancement of the biopsy needle into the patient. More commonly, the movement of the biopsy needle would be monitored independent of the diagnostic image. The image of the needle would be superimposed on the diagnostic image. As the needle moves, the superimposed images would be altered electronically to display the needle in the proper position. Various trajectory planning packages have been proposed which would enable the operator to plan the biopsy procedure in advance and electronically try various surgical paths through the 3D electronic data.

One of the disadvantages of the magnetic resonance system is that the surgery is either performed at field, i.e., in a high magnetic field, or the patient is moved back and forth between an imaging position in the field and a surgery position displaced from the field.

It has also been proposed to use a CT scanner rather than an MRI scanner to generate the diagnostic images in the operating room. However, when a CT scanner is operated to take a diagnostic image, the patient receives a significant dose of radiation. If the diagnostic imaging procedure were repeated numerous times to monitor the progress of a biopsy or other surgical procedure, the patient would be subject to a high cumulative radiation dose. Moreover, for surgeon and operator safety, the surgical procedure would be interrupted while the surgeon and other people present in the operating room moved behind x-ray opaque shields.

The present invention provides a new and improved imaging technique which overcomes the above-referenced problems and others.

SUMMARY OF THE INVENTION

In accordance with one aspect of the present invention, a CT scanner is provided. An x-ray source generates a cone-beam of radiation through a portion of an imaging volume. A two-dimensional detector array disposed across the imaging volume from the x-ray source receives x-rays which have traversed the imaging volume and converts those x-rays into digital data. A rotary drive rotates at least the x-ray source around the imaging volume and a linear drive moves the patient support and the x-ray source longitudinally relative to each other. In this manner, the cone-beam of radiation traverses a spiral around the imaging volume. A reconstruction processor reconstructs the data from the two-dimensional array into a volumetric image representation which is stored in a volumetric diagnostic image memory. A memory access circuit accesses the diagnostic image memory to withdraw selected image data for display on a human-readable monitor.

In accordance with a more limited aspect of the present invention, an x-ray source control selectively (1) causes the x-ray source to produce x-rays of one of a higher intensity and a lower intensity or (2) gates the x-ray source ON and OFF.

In accordance with another aspect of the present invention, an invasive surgical instrument is disposed adjacent the imaging volume. A volumetric diagnostic image of a portion of the subject in the imaging volume is generated with the higher intensity x-rays. An image of the invasive surgical instrument is generated with the lower intensity x-rays.

In accordance with another aspect of the present invention, the image of the surgical instrument is stored in a three-dimensional instrument memory which is continuously updated. The instrument image is superimposed on the diagnostic image such that the movement of the surgical instrument through the imaging volume is monitored in real time.

In accordance with another aspect of the present invention, a method of diagnostic imaging is provided. A fan-beam of radiation is rotated and longitudinally displaced around an imaging region such that an apex of the cone-beam moves in a helical path relative to the imaging region. The cone-beam of radiation is detected and converted into a two-dimensional array of image data. The image data is reconstructed into a volumetric image representation of a portion of the subject in the imaging region. A portion of the volumetric image representation is read out and converted into a human-readable display.

In accordance with a more limited aspect of the present invention, the volumetric image representation is read out concurrently with the rotating, detecting and reconstructing steps such that the volumetric image representation is updated and read out in real time.

In accordance with another aspect of the present invention, a surgical instrument is moved into the imaging region. Additional electronic image data of the instrument is generated and reconstructed into an image representation of the instrument. Corresponding portions of the subject image representation and the instrument image representation are read out, superimposed, and converted into a human-readable display.

One advantage of the present invention is that images are generated in real time.

Another advantage of the present invention is that it generates cine type imaging sequences.

Another advantage of the present invention resides in its low radiation doses.

Yet another advantage of the present invention is that it is compatible with images from x-ray fluoroscopy, CT, MR, nuclear, and ultrasound imaging techniques.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

The FIGURE is a diagrammatic illustration of an imaging system in accordance with the present invention.

DETAILED DESCRIPTION OF THE PREFERRED EMBODIMENT

A volume CT scanner assembly 10 includes an x-ray tube 12 which generates a cone beam 14 of radiation. After passing through an imaged region of a subject, the cone beam of radiation strikes a two-dimensional detector array 16. The two-dimensional detector array preferably includes a two-dimensional array of detector elements, each of which converts an intensity of received radiation into a corresponding data signal. The x-ray tube 12 and the radiation detector 16 are mounted to a common gantry 18. A motor 20 rotates the gantry, preferably continuously. A position encoder 22 provides a series of output positions indicative of the angular position of the x-ray source and detector relative to the imaged region during the rotation.

A subject is positioned on a patient support or couch 24. A drive motor 26 moves the patient support 24 and the gantry 18 longitudinally relative to each other. When the motor 26 moves the patient support, the patient support is readily positioned for convenient access and egress by the patient. On the other hand, when the motor 26 is mounted to move the gantry 18 relative to the patient support, the patient support remains stationary during scanning to simplify an interventional surgical procedure being performed on the patient. Preferably, the motor 26 causes cyclic, back and forth longitudinal movement between the patient support and the gantry during imaging such that the cone-beam of radiation traverses a spiral or helix relative to the patient. When the cyclic longitudinal movement is short, the patient can be imaged concurrently with an on-going interventional procedure. In this manner, a longitudinally elongated imaging region 28 is defined.

An image reconstruction processor array 30 reconstructs the electronic data from the detector array 16 into a volume image representation which is stored in a volumetric subject image memory 32. In the preferred embodiment, the detector array 16 is a two-dimensional rectangular grid of detectors. The detectors in each line perpendicular to the axis of the patient effectively detect a single slice. Of course, during the rotational and longitudinal motion, the slice moves along a helical path. A preprocessing circuit 34 performs filtering and other conventional preprocessing on the data from the detector and sorts the detector by slice to individual reconstruction processors $30_1, 30_2, \ldots, 30_n$ of the reconstruction processor array 30. Each of the processors stores the reconstructed image information in the same volume memory 32. It is to be appreciated that each reconstruction processor reconstructs data from spiral regions which overlap the regions reconstructed by the other processors. Reconstructed data from the plurality of the processors is combined to produce each pixel of the resultant volume image. To facilitate multiple access to the same volume memory, the volume memory is preferably a high speed, multi-access video memory. Buffers for temporarily storing data from each processor to prevent two processors from writing to the same memory cells simultaneously are contemplated. Suitable reconstruction algorithms for reconstructing the data from the spiral CT scanner assembly into three-dimensional volume diagnostic images are illustrated in U.S. Pat. Nos. 5,396,418, 5,485,493, and 5,544,212 and U.S. application Ser. No. 08/497,296. Other divisions of the data among multiple reconstruction processors are also contemplated.

For interventional surgery, additional three-dimensional diagnostic images are generated. More specifically to the preferred embodiment, three-dimensional images of the surgical instrument are generated, which images are superimposed on the diagnostic image. Because the interventional surgical instruments are generally constructed of metal or other materials with relatively high x-ray stopping power, and because the instruments are relatively simple in shape and much less structurally complex than the human anatomy, a much lower resolution x-ray imaging technique can be utilized. More specifically to the preferred embodiment, an x-ray tube control 40 gates the x-ray tube 12 ON and OFF at selected intervals. In the preferred embodiment, the x-ray tube is gated ON and OFF about 12 times per second. When the gantry 18 is rotating at a half second per revolution, the x-ray tube is gated ON about every 60° around the subject. Moreover, the x-ray tube control 40 runs the x-ray tube at a significantly lower power setting. The power setting is selected at the lowest possible power which still provides adequate resolution for reconstructing a three-dimensional image representation of the selected surgical tool.

A surgical tool 42, such as a biopsy needle guide 44 and biopsy needle 46 are mounted to the patient support. Appropriate mechanical interconnections are provided such that the guide can be positioned at any one of a large plurality of angular orientations and such that the entry point (typically one end of the guide) is freely selectable around the subject. A motion detector 48 is mounted in association with the biopsy needle to monitor when the needle is moving. A motion dependent x-ray tube gating control circuit 50 stops the x-ray tube control 40 from gating the x-ray tube ON when there has been no motion of the surgical tool for a selected duration, e.g., a second. Moreover, the gating control 50 determines recent rates of movement of the surgical instrument. When the instrument is being moved slowly, the gating control 50 causes the control circuit 40 to gate the x-ray tube ON less often, e.g., blocks the x-ray tube from being gated ON at every other 60° position.

Each time the x-ray tube is gated ON, the preprocessing circuit 34 samples the x-ray detector array and provides the data to the array of reconstruction processors. Optionally, a threshold filter 52 filters the data. More specifically, this reconstruction process is seeking to reconstruct an image of the surgical instrument alone, for superposition on the anatomical information. Reconstructing anatomical information is disadvantageous because it would create superfluous information for superimposition on the higher resolution previously generated anatomical diagnostic images. Accordingly, the threshold is set such that x-rays which do not pass through the surgical instrument have output values which are set to a zero or baseline data value. The array of reconstruction processors 30 reconstruct a three-dimensional image representation of the surgical instrument, which image representation is updated each time the x-ray tube is gated ON, about every $1/12$ second. The most recently reconstructed instrument image representation is stored in a volumetric instrument image memory 54.

As another option, the x-ray tube can be pulsed at 60° or other intervals at full power to generate physiological diagnostic data for updating the physiological volume memory 32. Updating of the physiological data memory will find application, for example, in procedures to remove a blockage in the circulatory system or other interventional procedures which result in an x-ray measurable physiological change.

A threshold circuit 56 removes any reconstructed physiological, artifacts, or other information not attributable to the instrument on the reconstructed image in the instrument memory. A trajectory circuit 58 calculates the trajectory of the surgical instrument. Returning again to the biopsy needle example, the position of the biopsy needle in the guide fixes its trajectory to a straight line. The trajectory circuit projects the straight line followed by the center of the biopsy needle and creates a trajectory display, e.g., a dashed line or a line in a different color extending from the front of the biopsy needle.

A diagnostic image selection processor 60 is utilized by the operator to select the nature of the displayed image. For example, the operator may select a slice through the patient to be displayed, a slice parallel to the trajectory, a slice(s) orthogonal to the trajectory, a set of coordinated slices along three orthogonal axes, a slice through a curved cutting plane, a three-dimensional rendering, or the like, as are known in the art. The image selection circuit 60 causes a pair of memory reading circuits 62a, 62b to read the image data from the corresponding voxels of the diagnostic image memory 32 and the instrument volume memory 54. An image superimposing circuit 64 combines the physiological image, the instrument image, and trajectory. A video processor 66 converts the combined images into the appropriate format for display on a video monitor 68. Preferably, a trackball 70 or other data input device is connected with the image selection processor 60 to enable the operator to rapidly change between selected slices, slice orientations, or the like.

Preferably, the trajectory circuit 58 projects the trajectory and provides a distance gauge. More specifically, from the known dimensions of the CT scanner system 10, the trajectory circuit determines distance, e.g., in millimeters, along the trajectory. Using the trackball 70, the operator designates a point along the trajectory and the projection circuit determines a distance from the end of the biopsy needle or other surgical device to the designated point and displays such distance on the video monitor 68.

As another option, the image selector 60 further enables the operator to select and designate a target physiological structure. More specifically, the image selection circuit calls up selected slice or other images. The operator uses the trackball to move a cursor to a physiological structure which is the target, e.g., a tumor to be biopsied. The CT number of the designated target voxel is retrieved by the image selector processor 60. A region growing circuit 80 compares each adjacent voxel to the designated target voxel of the physiological image memory with the retrieved CT number to determine whether it has substantially the same CT number. By checking adjacent voxels to each voxel with substantially the same CT number, the region growing processor 80 determines a group of voxels, in three dimensions, which all have substantially the same CT number. Tissue with the same CT number is assumed, subject to operator override, to be a common physiological entity. A target colorizing circuit 82 causes the pixels designated by the region growing processor 80 to be displayed in a unique color. In this manner, the target physiological entity is readily identified for the surgeon.

In order to insure alignment between the patient and the instrument images, a plurality of radiation opaque markers are preferably affixed to the patient. These markers, such as three metal beads, show up clearly in both the physiological and the instrument reconstructed image. Because the material with which the beads are constructed is known, their radiation absorption properties are known. Hence, the physiological and instrument images are readily thresholded to locate the markers. An image alignment processor 72 compares the position of the markers in the two images. If the image alignment algorithm finds that the markers are out of alignment, it adjusts the addresses read by the memory reading circuit 62a and 62b with the appropriate offset or rotation. In this manner, the instrument image is automatically kept aligned with the image data, even if the subject moves.

The use of these markers enables the physiological diagnostic image to be taken at a different time or place than the image of the instrument. Similarly, markers which are visible in other imaging modalities as well as x-rays enable the diagnostic images to be generated with other types of imaging apparatus such as magnetic resonance, ultrasound, nuclear, x-ray, and other types of imagers. Analogously, the diagnostic images generated with other imaging modalities may be stored in a third volume memory. The image control 60 then causes corresponding images to be withdrawn from the volume memory for the other imaging modality concurrently with the other images for concurrent display. The instrument image can be superimposed on the other imaging modality diagnostic image as well as the spiral CT diagnostic image.

Additional memory reading circuits, video circuits and monitors can be provided to provide multiple images to the surgeon at the surgical site, as well as to provide images at a remote site.

As another option, the diagnostic memory 32 is enlarged to store four dimensions of data, time being the fourth dimension. In this manner, a series of time displaced images of the same volumetric region are generated and stored. The operator can then display the series of time displaced images of a common selected slice or other display format in a cine format. Such time dependent, cine imaging is particularly advantageous with angiography.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A CT scanner comprising:

and x-ray source for generating a low energy cone-beam of radiation through an imaging volume;

a two-dimensional detector array disposed across the imaging volume from the x-ray source for receiving x-rays which have traversed the imaging volume and converting the x-rays into digital data;

a rotary drive for rotating at least the x-ray source around the imaging volume and a linear drive for moving a patient support and the x-ray source longitudinally relative to each other;

a control which coordinates the rotary drive and the linear drive such that the cone-beam of radiation traverses a spiral around and along the imaging volume;

a reconstruction processor for reconstructing image data from the two-dimensional array;

a volumetric, diagnostic image memory which is continuously updated with the reconstructed image data from the reconstruction processor to store a continuously updated volumetric image representation;

a memory access circuit for accessing the diagnostic image memory to withdraw selected portions of the continuously updated volumetric image representation to generate a continuously updated real-time display on a human-readable monitor; and an x-ray source control for selectively causing the x-ray source to produce x-rays of a preselected lower intensity in a fluoroscopic mode of operation.

2. The apparatus as set forth in claim 1 further including:

a plurality of reconstruction processors connected in parallel, the plurality of reconstruction processors reconstructing a common volumetric image representation for storage in the volumetric, diagnostic image memory;

a preprocessing circuit for dividing the digital data from the two-dimensional detector array among the reconstruction processors.

3. A CT scanner comprising:

an x-ray source for generating a cone-beam of radiation through an imaging volume;

a two-dimensional detector array disposed across the imaging volume from the x-ray source for receiving x-rays which have traversed the imaging volume and converting the x-rays into digital data;

a rotary drive for rotating at least the x-ray source around the imaging volume and a linear drive for moving a patient support and the x-ray source longitudinally relative to each other such that the cone-beam of radiation traverses a spiral around the imaging volume;

a reconstruction processor for reconstructing image data from the two-dimensional array into a volumetric image representation;

a volumetric, diagnostic image memory for storing the volumetric image representation;

a memory access circuit for accessing the diagnostic image memory to withdraw selected image data therefrom for display on a human-readable monitor;

an x-ray source control for selectively causing the x-ray source to produce x-rays of a first, preselected higher intensity and a second, preselected lower intensity; and an invasive surgical instrument disposed at the imaging volume, the first, higher intensity x-rays being of an appropriate intensity to generate diagnostic image data of a portion of a patient disposed in the imaging region and the second, selected lower intensity being appropriate for generating a three-dimensional image of the surgical instrument.

4. The apparatus as set forth in claim 3 further including:

a three-dimensional instrument memory for storing a three-dimensional image of the instrument;

a memory access circuit for accessing selected image data from the three-dimensional instrument memory;

an image combining circuit for superimposing images retrieved from the instrument memory and the diagnostic image memory to generate an image of the surgical instrument superimposed on the diagnostic image.

5. The apparatus as set forth in claim 4 further including:

a trajectory processor for determining a trajectory of the surgical instrument from the three-dimensional image representation of the surgical instrument stored in the instrument memory and generating trajectory image data which is supplied to the image combining circuit such that the trajectory is displayed superimposed on the image.

6. The apparatus as set forth in claim 4 further including:

at least three alignment elements which are affixed to the subject and reconstructed in both the instrument image and the diagnostic image;

an alignment processor for aligning the instrument and diagnostic images such that the alignment elements are substantially superimposed.

7. A CT scanner comprising:

an x-ray source for generating a cone-beam of radiation through an imaging volume;

a two-dimensional detector array disposed across the imaging volume from the x-ray source for receiving x-rays which have traversed the imaging volume and converting the x-rays into digital data;

a rotary drive for rotating at least the x-ray source around the imaging volume and a linear drive for moving a patient support and the x-ray source longitudinally relative to each other such that the cone-beam of radiation traverses a spiral around the imaging volume;

a reconstruction processor for reconstructing image data from the two-dimensional array into a volumetric image representation;

a volumetric, diagnostic image memory for storing the volumetric image representation;

a memory access circuit for accessing the diagnostic image memory to withdraw selected image data therefrom for display on a human-readable monitor;

an x-ray source control for selectively causing the x-ray source to produce x-rays of a first, preselected higher intensity and a second, preselected lower intensity; and an x-ray tube control for selectively gating the x-ray tube ON and OFF at intervals, whereby a subject in the imaging area is only subject to intermittent radiation.

8. The apparatus as set forth in claim 7 further including:
a position encoder for determining an angular position of the x-ray tube as it rotates around the imaging region, the position encoder enabling the x-ray tube control to gate the x-ray tube ON at periodic angular increments around the imaging area.

9. A CT scanner comprising:
an x-ray source for generating a cone-beam of radiation through an imaging volume;
a two-dimensional detector array disposed across the imaging volume from the x-ray source for receiving x-rays which have traversed the imaging volume and converting the x-rays into digital data;
a rotary drive for rotating at least the x-ray source around the imaging volume and a linear drive for moving a patient support and the x-ray source longitudinally relative to each other such that the cone-beam of radiation traverses a spiral around the imaging volume;
a reconstruction processor for reconstructing image data from the two-dimensional array into a volumetric image representation;
a volumetric, diagnostic image memory for storing the volumetric image representation;
a memory access circuit for accessing the diagnostic image memory to withdraw selected image data therefrom for display on a human-readable monitor;
an x-ray source control for selectively causing the x-ray source to produce x-rays of a first, preselected higher intensity and a second, preselected lower intensity;
an image selection circuit which controls the memory access circuits to select an image for display;
a cursor control for positioning a cursor on a selected voxel of the displayed image;
a region growing processor for examining voxels surrounding an identified target voxel to locate contiguous voxels with like image values; and
a colorization circuit for causing data from the voxels of like image value to be displayed in a distinctive color, whereby a selected target is displayed in an identifiable color.

10. A method of diagnostic imaging comprising:
rotating and longitudinally displacing a cone-beam of radiation around an imaging region such that an apex of the cone-beam moves in a helical path;
detecting the cone-beam radiation and converting it into electronic image data indicative of a two-dimensional array of image data, which two-dimensional array of image data rotates with the cone-beam of radiation;
reconstructing the electronic image data into a volumetric image representation of a portion of a subject in the imaging region;
reading out a portion of the volumetric image representation and converting the read out portion into a human-readable display;
continuing the rotation of the cone-beam of radiation along the spiral path around the imaging region for a selected duration;
during the selected duration, reconstructing the image data into a temporally displaced series of volumetric images; and
displaying a corresponding selected region of each of the temporally displaced volumetric images sequentially on a human-readable display to generate a cine type display illustrating changes in the imaging volume with time.

11. A method of diagnostic imaging comprising:
rotating and longitudinally displacing a cone-beam of radiation around an imaging region such that an apex of the cone-beam moves in a helical path;
detecting the cone-beam radiation and converting it into electronic image data indicative of a two-dimensional array of image data, which two-dimensional array of image data rotates with the cone-beam of radiation;
reconstructing the electronic image data into a volumetric image representation of a portion of a subject in the imaging region;
reading out a portion of the volumetric image representation and converting the read out portion into a human-readable display;
identifying a voxel of the human-readable display as a target area;
examining contiguous voxels of the three-dimensional image for voxels of like material; and
displaying the contiguous voxels of like material in a distinctive color on the human-readable display such that a target material within the subject is denoted in the displayed images by color.

12. A method of fluoroscopic imaging comprising:
rotating and longitudinally displacing a low energy cone-beam of radiation around an imaging region such that an apex of the cone-beam moves back and forth along a helical path;
detecting the cone-beam radiation and converting it into electronic projection data indicative of a two-dimensional array of projection data, which two-dimensional array of projection data rotates with the cone-beam of radiation;
reconstructing the electronic projection data to update a volumetric image representation of a portion of a subject in the imaging region;
reading out a portion of the volumetric image representation concurrently with the rotating, detecting, and reconstructing steps such that the volumetric image representation is continuously updated and concurrently read out in real time during updating of the volumetric image representation; and
converting the read out portion into a human-readable display which is continuously updated.

13. A method of diagnostic imaging comprising:
rotating and longitudinally displacing a cone-beam of radiation around an imaging region such that an apex of the cone-beam moves along a helical path;
detecting the cone-beam radiation and converting it into electronic data indicative of a two-dimensional array of data, which two-dimensional array of data rotates with the cone-beam of radiation;
reconstructing the electronic data into a volumetric image representation of a portion of a subject in the imaging region;
reading out a portion of the volumetric image representation and converting the read out portion into a human-readable display;
moving a surgical instrument into the imaging region;
continuing rotating the cone beam of radiation around the imaging region to generate additional electronic data;
reconstructing the additional image data into a volumetric image representation of the instrument;
reading out a portion of the image volumetric representation corresponding to the read out portion subject volumetric image representation and converting the read out portion into a human-readable instrument display; and superimposing the read out portions of the instrument and patient volumetric image representations in the human-readable display.

14. The method as set forth in claim 13 wherein when generating the additional image data, the cone-beam of radiation is gated ON and OFF periodically as the cone-beam rotates around the imaging region to update the volumetric instrument representation, whereby the human-readable display of the subject image and superimposed surgical instrument reflects real time movement of the surgical instrument through the imaging region of the subject.

15. The method as set forth in claim 13 further including:
reducing an intensity of the cone-beam of radiation during the generation of the additional image data.

16. The method as set forth in claim 13 further including:
from the volumetric instrument image representation, determining a trajectory of the instrument;
superimposing the generated trajectory on the human-readable display.

\* \* \* \* \*